(12) United States Patent
Hoseit

(10) Patent No.: US 10,987,492 B2
(45) Date of Patent: Apr. 27, 2021

(54) IMAGING GUIDEWIRE WITH PHOTOACTIVATION CAPABILITIES

(71) Applicant: VOLCANO CORPORATION, San Diego, CA (US)

(72) Inventor: Paul Hoseit, El Dorado Hills, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1236 days.

(21) Appl. No.: 14/132,479

(22) Filed: Dec. 18, 2013

(65) Prior Publication Data

US 2014/0180056 A1 Jun. 26, 2014

Related U.S. Application Data

(60) Provisional application No. 61/740,556, filed on Dec. 21, 2012.

(51) Int. Cl.
*A61B 8/12* (2006.01)
*A61M 25/09* (2006.01)
(Continued)

(52) U.S. Cl.
CPC .......... *A61M 25/09* (2013.01); *A61B 5/0095* (2013.01); *A61B 5/6851* (2013.01); *A61B 5/6852* (2013.01); *A61B 8/12* (2013.01); *A61B 8/445* (2013.01); *A61B 8/4483* (2013.01); *A61N 5/062* (2013.01); *G01S 15/8965* (2013.01); *G01S 15/8968* (2013.01);
(Continued)

(58) Field of Classification Search
CPC ... A61B 5/6851; A61B 5/6852; A61B 5/0095; A61M 25/09; A61M 2025/09175; A61M 2025/09075; A61M 2025/09133; A61N 5/062; A61N 2005/063; G01S 15/8965; G01S 15/8968
See application file for complete search history.

(56) References Cited

U.S. PATENT DOCUMENTS 5,368,035 A * 11/1994 Hamm ................. A61B 5/6848
600/439
6,176,842 B1 1/2001 Tachibana et al.
(Continued)

FOREIGN PATENT DOCUMENTS

WO WO 2006/061829 6/2006

OTHER PUBLICATIONS

Kwitnieski et al., "Immunotherapy: a way to improve the therapeutic outcome of photodynamic therapy?" Photochem. Photobiol. Sci., 2008, 7, 1011-1017.*
(Continued)

*Primary Examiner* — Katherine L Fernandez
*Assistant Examiner* — Colin T. Sakamoto

(57) ABSTRACT

A guidewire providing imaging and light for photoactivation of therapeutic agents. Using optical fibers with Bragg gratings, electromagnetic waves are coupled to photoacoustic materials thereby providing acoustic energy for imaging tissues. The reflected acoustic waves can be sensed with photoreflective materials coupled to different optical fibers. Additional optical fibers allow photoactivated therapeutics to be activated in proximity to the imaged tissues. The photoactivated therapeutics may be administered intravenously or with a drug-delivery catheter.

29 Claims, 7 Drawing Sheets

(51) Int. Cl.
*A61N 5/06* (2006.01)
*A61B 5/00* (2006.01)
*G01S 15/89* (2006.01)
*A61B 8/00* (2006.01)

(52) U.S. Cl.
CPC ............ *A61M 2025/09075* (2013.01); *A61M 2025/09133* (2013.01); *A61M 2025/09175* (2013.01); *A61N 2005/063* (2013.01)

(56) References Cited

U.S. PATENT DOCUMENTS

| | | | |
|---|---|---|---|
| 7,153,299 B1 | 12/2006 | Tu et al. | |
| 2003/0219202 A1 | 11/2003 | Loeb et al. | |
| 2004/0067000 A1* | 4/2004 | Bates .................... | G01H 9/004 |
| | | | 385/7 |
| 2004/0082844 A1 | 4/2004 | Vardi et al. | |
| 2006/0241572 A1* | 10/2006 | Zhou .................... | A61B 8/4483 |
| | | | 606/7 |
| 2007/0206193 A1 | 9/2007 | Pesach | |
| 2008/0108867 A1* | 5/2008 | Zhou .................... | A61B 8/4483 |
| | | | 600/104 |
| 2008/0114254 A1* | 5/2008 | Matcovitch ............. | A61B 8/12 |
| | | | 600/463 |
| 2008/0177145 A1* | 7/2008 | Furnish ................ | A61B 5/0075 |
| | | | 600/178 |
| 2008/0177183 A1 | 7/2008 | Courtney et al. | |
| 2011/0144502 A1 | 6/2011 | Zhou et al. | |

OTHER PUBLICATIONS

International Search Report and Written Opinion received in Patent Cooperation Treaty Application No. PCT/US13/76173, dated Mar. 11, 2014, 10 pages.

\* cited by examiner

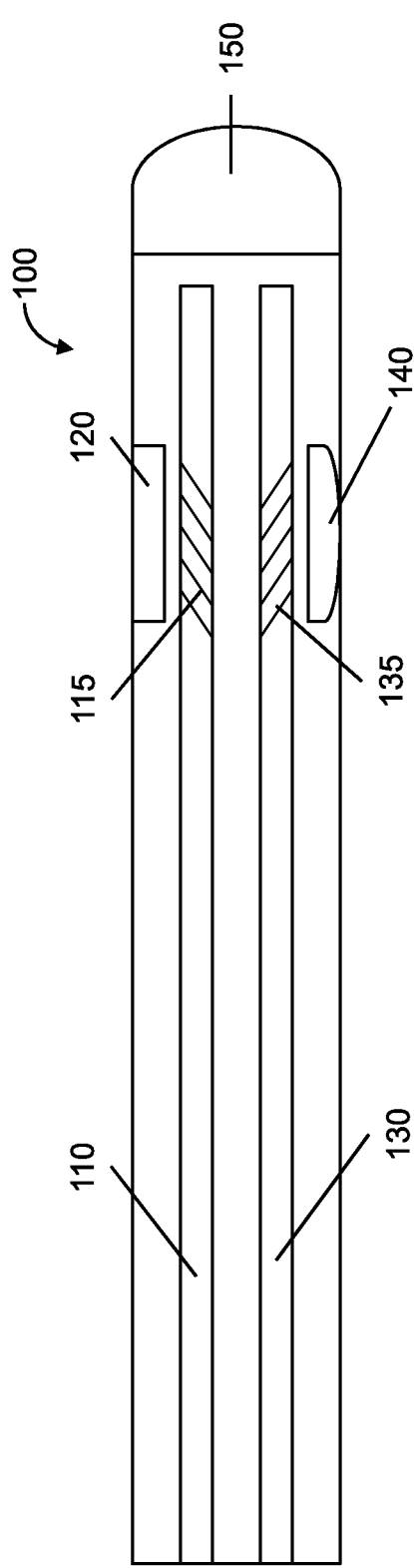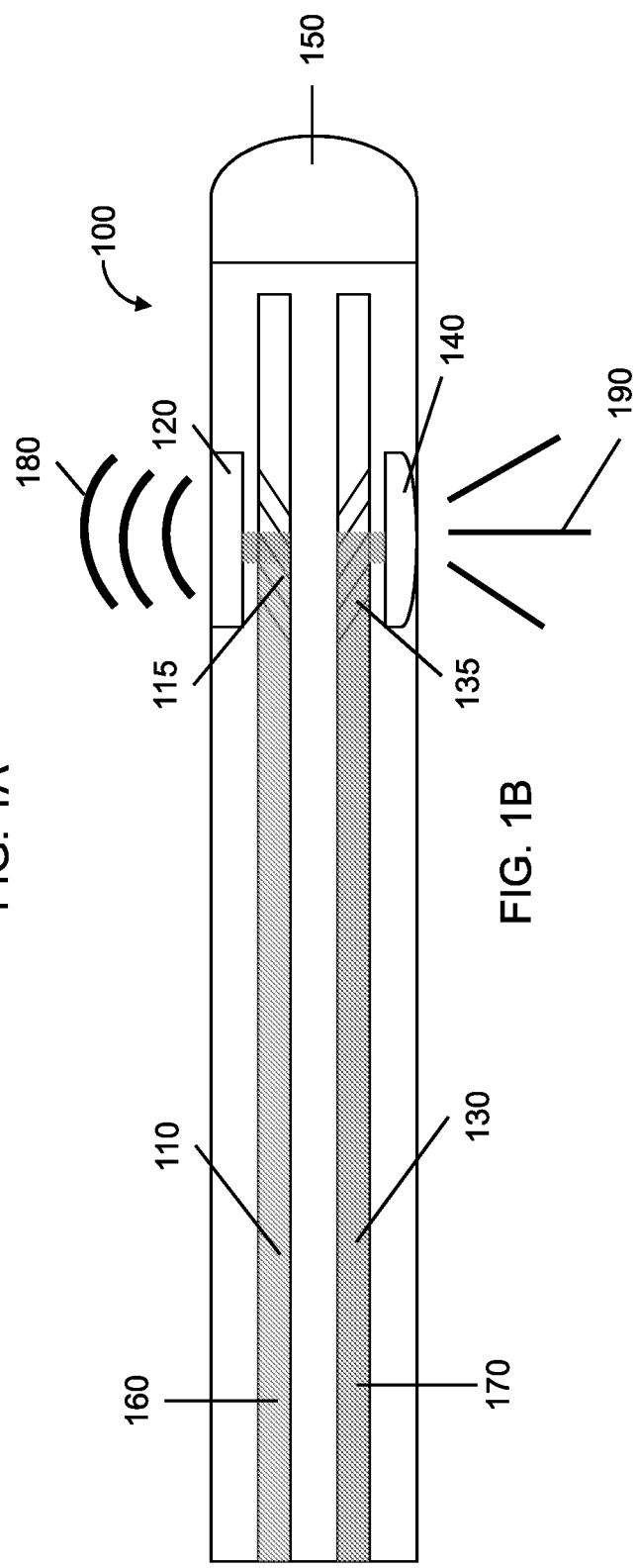

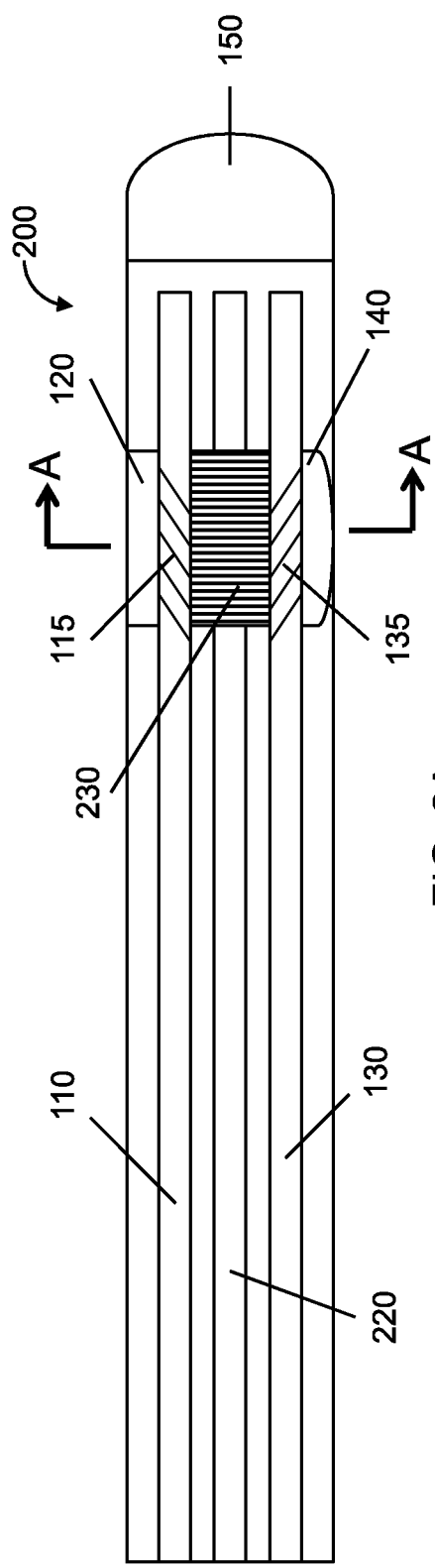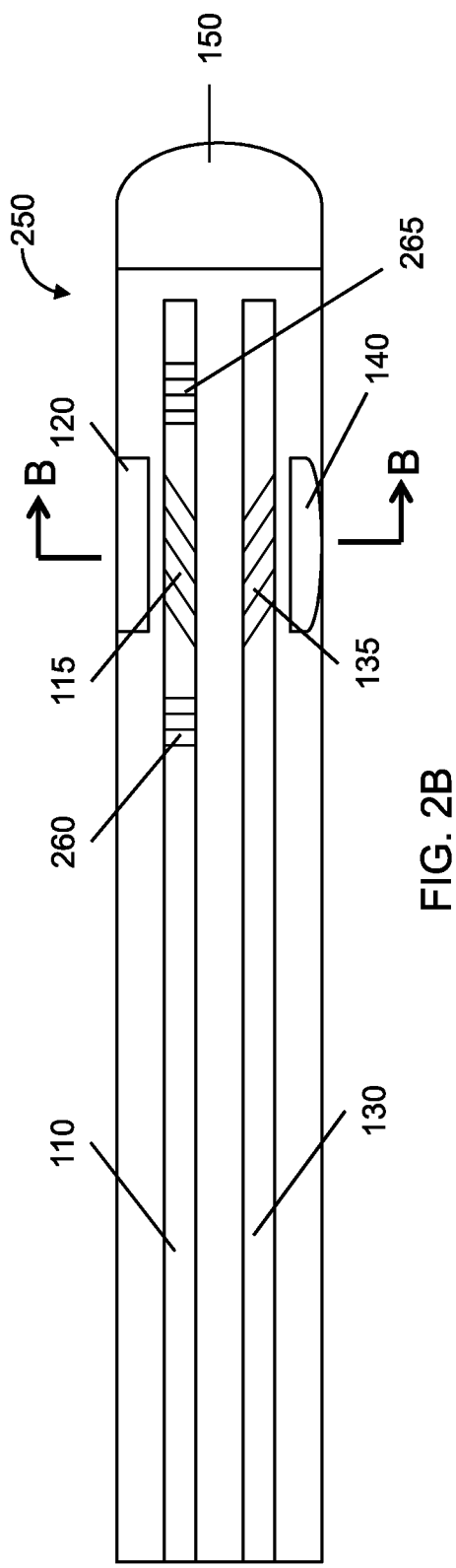
FIG. 2A
FIG. 2B

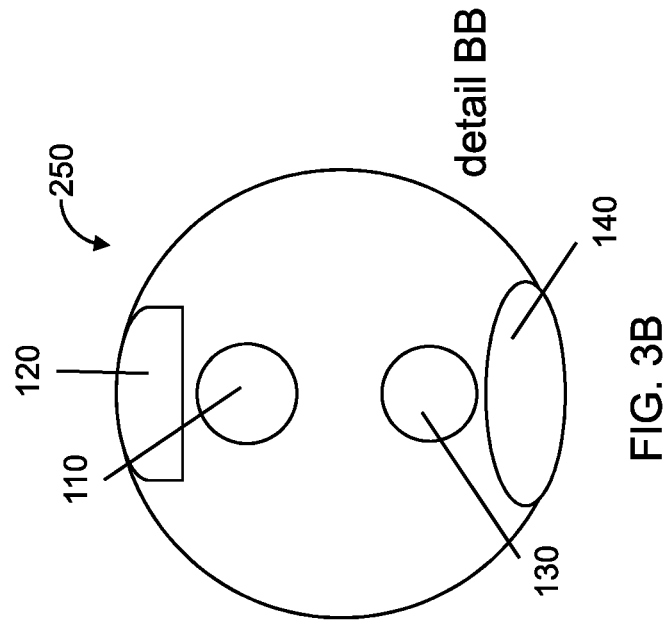
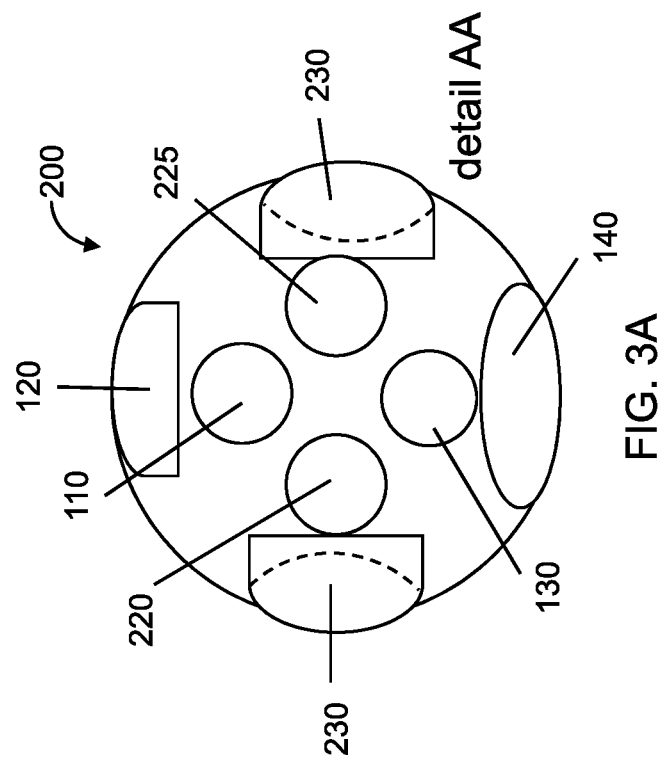

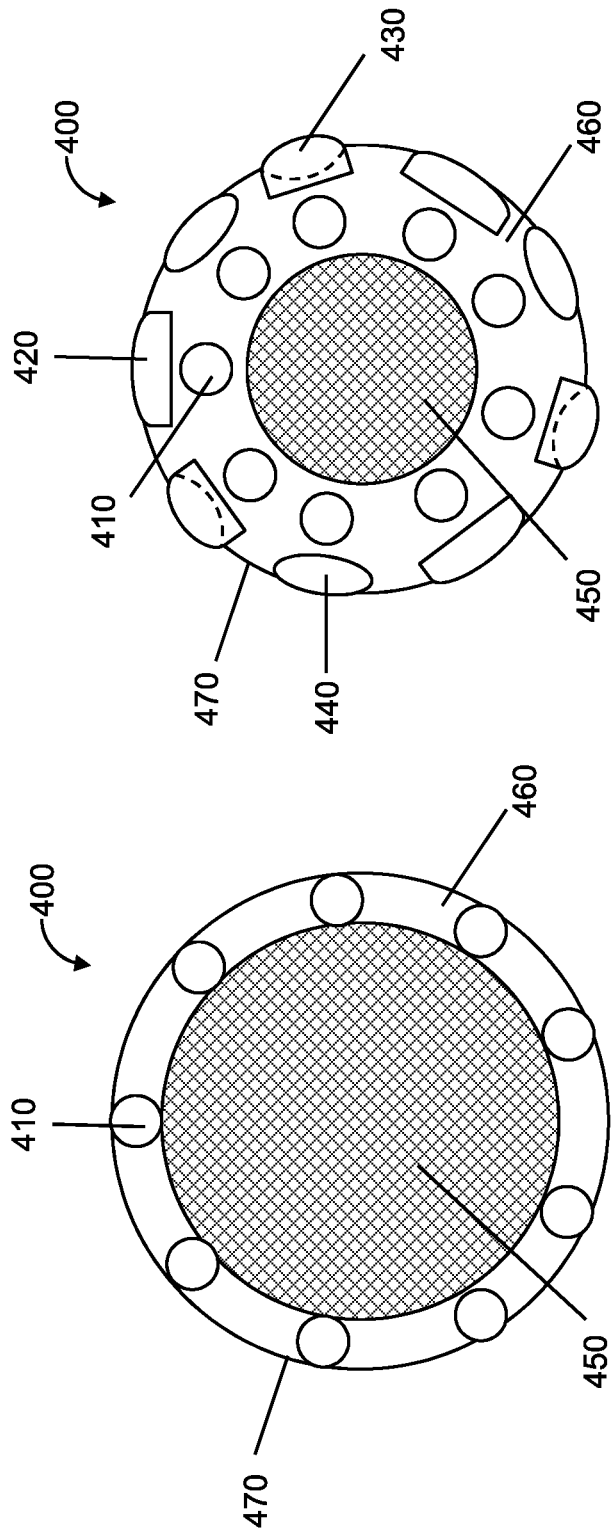

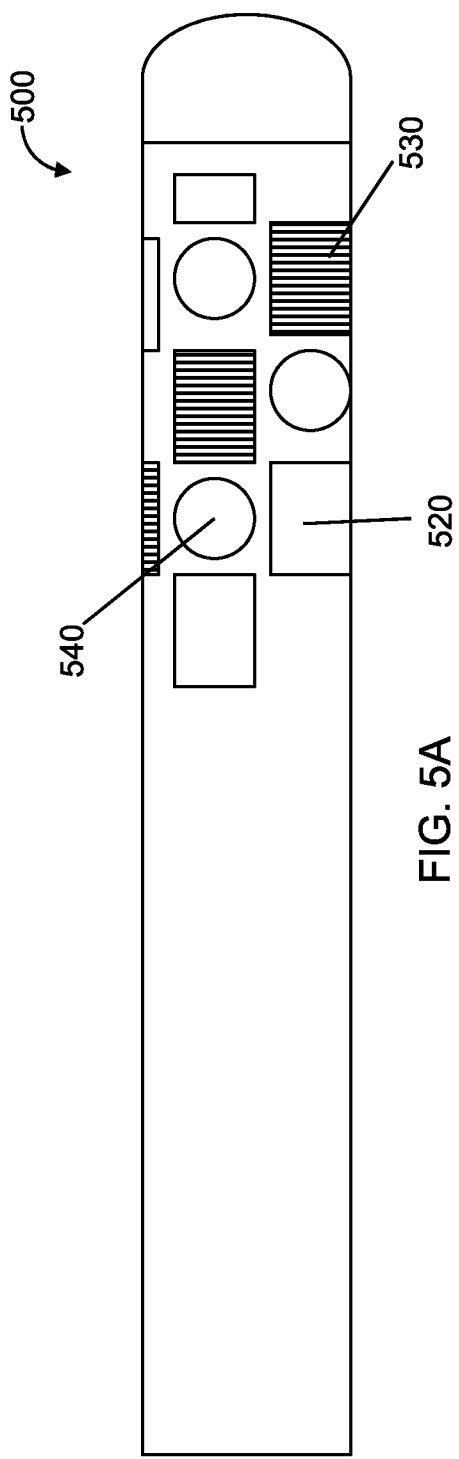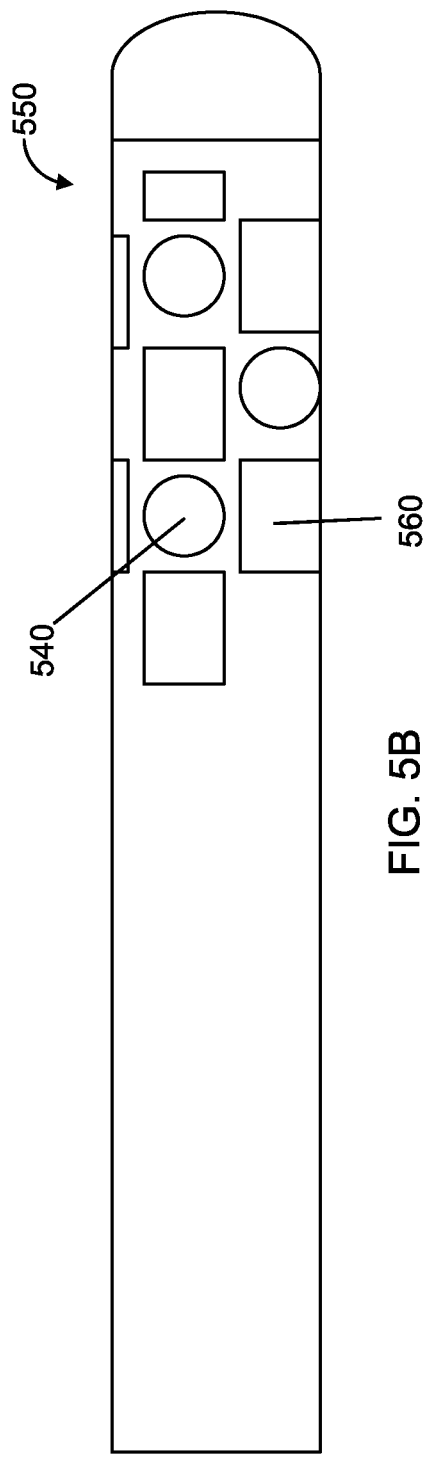
FIG. 5A
FIG. 5B

IMAGING GUIDEWIRE WITH PHOTOACTIVATION CAPABILITIES

RELATED APPLICATION

This application claims the benefit of and priority to U.S. Provisional Ser. No. 61/740,556, filed Dec. 21, 2012, which is incorporated by reference in its entirety.

FIELD OF THE INVENTION

The invention relates to guidewires used in medical procedures, such as endovascular imaging and therapy. The invention provides guidewires, methods and systems for imaging structures within a subject and delivering light therapy, such as used to activated photosensitive therapeutic agents.

BACKGROUND

The effectiveness of a therapeutic agent, i.e., a drug, is limited by the ability to deliver the therapeutic to a targeted tissue at an effective concentration. For example, certain chemotherapeutic agents are very effective at halting the growth of rapidly dividing cells (e.g., malignant tumors) but the same drugs attack other "normal" rapidly dividing cells. Accordingly, the agents cannot be administered intravenously at the maximum effective dose because this dose will also irreparably harm healthy systems, such as the small intestine. Other classes of therapeutics based on biological molecules (e.g., interfering ribonucleic acids RNAi), are metabolized by the body upon administration, making it difficult to deliver the therapeutic to targeted organs or tissues at a concentration sufficient to be effective. Still other types of agents are difficult to deliver because they are not water soluble, or are otherwise incompatible with biological systems.

Drug delivery advances have overcome many of these problems, however, there is still a need for improved methods of delivering therapeutic agents. For example, the chemical structure of some therapeutics can be modified to improve the solubility or metabolic characteristics, making it possible to deliver the therapeutic orally or intravenously. Yet, in some cases, modifying the chemical structure deactivates the therapeutic or increases the toxicity. In the instance where the active cannot be modified, a delivery formulation may be created for administration, e.g., a lipid formulation, however, the formulations can interfere with the effectiveness of the drug.

One alternative to modifying or reformulating therapeutics is to directly deliver the therapeutic to the tissue, i.e., not administering the therapeutic orally or intravenously. For certain tissues, this is rather straightforward. For example, the therapeutic can be directly administered to the skin, mouth, intravaginally, etc. For other tissues, direct administration requires an open surgical field to access the tissue and administer the therapeutic. While techniques such as chemotherapy organ baths have been used, these techniques are experimental and only used as last resort when conventional methods have failed. In addition to the possible complications of the surgical procedure, organ baths can actually spread the cancer by dislodging cells that can start new tumors on other tissues.

In the field of cardiology, drug delivery catheters have been used for some time to deliver therapeutics, e.g., thrombolytic drugs, directly to tissues needing treatment. Drug delivery catheters allow more concentrated dosing of thrombolytics in proximity to the thrombus while reducing the risk of damage to healthy tissues. Nonetheless, these techniques are limited by the size of the catheters and the functions that must be performed prior to and after delivery of the therapeutic.

Conventionally, a thrombus is identified using a contrast agent and fluoroscopy. Once identified, the distal end of a guidewire is placed in proximity to the thrombus and the drug delivery catheter is moved to the distal end of the guidewire whereupon the thrombolytic is administered. After administration the catheter is removed, and the treatment site is re-imaged, either with angiography or with a separate imaging catheter. Based upon the imaging, the drug-delivery procedure may need to be repeated. Thus, the conventional method takes a fair amount of time and the patient may be exposed to greater amounts of contrast and x-ray radiation due to post-procedural angiography. Additionally, drug delivery catheters can only be used to administer therapeutics to vasculature of a size sufficient to accept the catheter. Thus, if the site to be treated is occluded with plaque or if the vessel is a peripheral vessel, it may not be possible to deliver the therapeutic to the tissue.

SUMMARY

The disclosed invention—an imaging guidewire that delivers drug-activating light—solves several problems discussed above. First, the guidewire is quite small, on the order of 1 mm or smaller, allowing the guidewire to be placed throughout the vasculature, as well as the lymphatic, urological, and reproductive systems. Because of this versatility, the guidewire can be used to treat a number of organs, such as the kidneys, lungs, brain, heart, pancreas, ovaries, or testes. When coupled with photoactivated therapeutics, delivered intravenously, for example, it is possible to deliver targeted therapy, such as anti-cancer drugs, only to the tissues in need of treatment. Furthermore, because the therapy is localized a more potent dose can be delivered with fewer side effects.

Second, because the guidewire is capable of imaging and characterizing the treated tissues before and after therapy, treatment times can be shortened, reducing the amount anesthesia, contrast, and x-rays to which a patient is exposed. For example, in an endovascular procedure, the guidewire can be placed once using angiography, the treatment site imaged using the guidewire, the therapeutic administered (e.g., using a drug-delivery catheter) and activated with light from the guidewire, and the treatment site subsequently re-imaged with the guidewire to confirm the results of the treatment.

Third, when used in intravascular procedures, the disclosed guidewires will allow therapeutics to be administered beyond restrictions in the vasculature or to peripheral vasculature that cannot be accessed with standard-sized drug delivery catheters. The guidewire can placed in proximity to a tissue needing treatment, and then used to image the tissue. A mating drug-delivery catheter can then be placed as close as possible to the tissue and then an amount of photoactivated therapeutic can be allowed to flow to the tissue, whereupon it is activated by the light, resulting in treatment localized to the tissue.

The guidewires of the invention achieve their versatility by using a system of optical fibers bundled to a core. The design makes efficient use of optical Bragg gratings which work as partially or fully reflective wavelength selective elements. The optical fibers provide both imaging and photoactivating light because a portion of the fibers are coupled to photoacoustic transducers which convert electromagnetic radiation to acoustic energy, a portion of the fibers are coupled to acoustic-sensing materials, for example photoreflective material or a strain-gauge type arrangements, and a portion of the fibers are coupled to lenses allowing the light to photoactivate therapeutics exterior to the guidewire.

Accordingly, the invention is, among other things, a guidewire including a first optical fiber including a first blazed Bragg grating being at least partially reflective of a first wavelength, a photoabsorptive member that absorbs the first wavelength and is in photocommunication with the first blazed Bragg grating, a second optical fiber including a second blazed Bragg grating being at least partially reflective of a second wavelength, and a lens in photocommunication with the second blazed Bragg grating and an exterior of the guidewire. In one embodiment, the guidewire will also include either a third optical fiber including a third blazed Bragg grating being at least partially reflective of a third wavelength and a photoreflective member that reflects the third wavelength and is in photocommunication with the third blazed Bragg grating. In one embodiment, the first optical fiber includes a first and a second Bragg grating being at least partially reflective of the first wavelength, allowing the first optical fiber to act as an acoustic transducer and an acoustic sensor. In some embodiments, the functions are accomplished by two separate fibers, a first with a blazed Bragg grating and a photoacoustic material, providing the acoustic energy, and a second with two normal Bragg gratings acting as partially reflective materials and making possible the detection of acoustic energy reflected from the surrounding tissues. Normal denotes that the Bragg gratings are oriented perpendicular to the direction of propagation.

Additionally disclosed are methods of treating a subject, including imaging a subject with acoustic energy produced from a guidewire, administering a photosensitive therapeutic agent to the subject, and activating the photosensitive therapeutic agent with electromagnetic radiation from the guidewire. In some embodiments, the guidewire includes a first optical fiber comprising a first blazed Bragg grating being at least partially reflective of a first wavelength, a photoabsorptive member that absorbs the first wavelength and is in photocommunication with the first blazed Bragg grating, a second optical fiber including a second blazed Bragg grating being at least partially reflective of a second wavelength, and a lens in photocommunication with the second blazed Bragg grating and an exterior of the guidewire.

The invention additionally includes systems including the guidewires disclosed herein. Systems of the invention can include, for example, a guidewire of type described herein, a source of the first wavelength optically coupled to a first optical fiber of the guidewire, a source of the second wavelength optically coupled to a second optical fiber of the guidewire, and a controller coupled to the source of the first wavelength and the source of the second wavelength, and capable of imaging a portion of a subject with acoustic energy created with the first wavelength and activating a photosensitive therapeutic agent with the second wavelength. In some embodiments, the guidewire also includes either a third optical fiber including a third blazed Bragg grating being at least partially reflective of a third wavelength and a photoreflective member that reflects the third wavelength and is in photocommunication with the third blazed Bragg grating. In one embodiment, the first optical fiber includes a first and a second Bragg grating being at least partially reflective of the first wavelength, allowing the first optical fiber to act as an acoustic transducer and an acoustic sensor. In some embodiments, the functions are accomplished by two separate fibers, a first with a blazed Bragg grating and a photoacoustic material, providing the acoustic energy, and a second with two normal Bragg gratings acting as partially reflective materials and making possible the detection of acoustic energy reflected from the surrounding tissues. In some embodiments, the system will also include a drug delivery catheter.

BRIEF DESCRIPTION OF THE FIGURES

FIG. 1A depicts a distal end of an embodiment of a guidewire;

FIG. 1B depicts the simultaneous or sequential delivery of acoustic (curved lines) and electromagnetic waves (straight lines) from the distal end of the embodiment of a guidewire of FIG. 1A;

FIG. 2A depicts a distal end of an embodiment of a guidewire including a photoreflective material that allows reflected acoustic waves to be detected;

FIG. 2B depicts a distal end of an embodiment of a guidewire including normal Bragg gratings that allow the fiber to detect reflected acoustic waves;

FIG. 3A depicts a cross-sectional view of the distal end of the embodiment of a guidewire of FIG. 2A;

FIG. 3B depicts a cross-sectional view of the distal end of the embodiment of a guidewire of FIG. 2B;

FIG. 4A depicts a cross-section of a proximal end of an embodiment of a guidewire;

FIG. 4B depicts a cross-section of a distal end of an embodiment of a guidewire;

FIG. 5A depicts an array of photoacoustic transducers, photoreflective receivers, and lenses at a distal tip of an embodiment of a guidewire;

FIG. 5B depicts an array of combined photoacoustic transducers/acoustic detectors and lenses at a distal tip of an embodiment of a guidewire;

DETAILED DESCRIPTION

Figure 6:
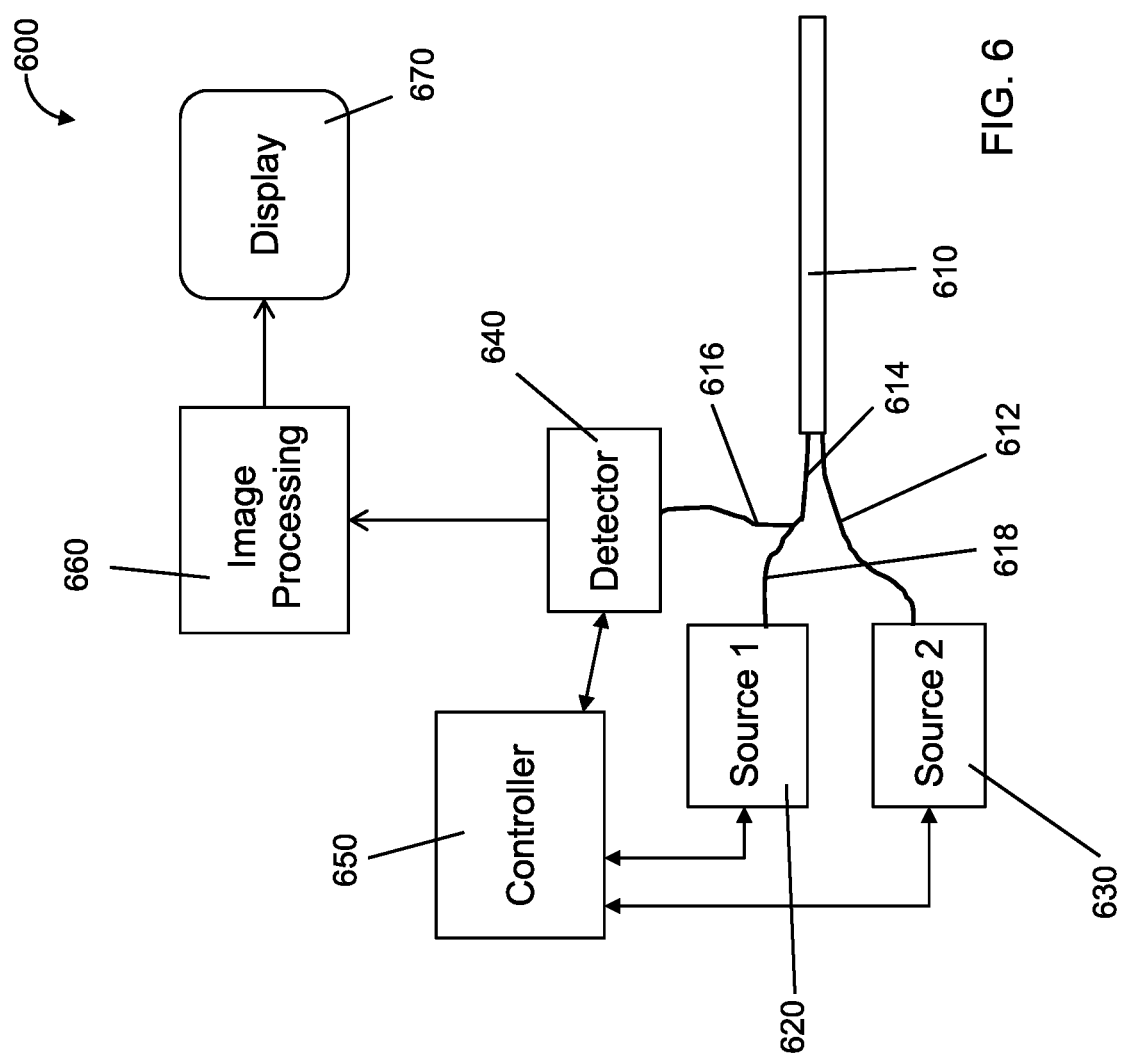
FIG. 6 depicts an embodiment of a system for ultrasound imaging and light therapy delivery with a guidewire.

The invention provides advanced guidewires that can be used to image tissues, such as vasculature, and also to deliver light therapy, for example to activate photosensitive therapeutics. Once the guidewire is placed near a feature to be treated, e.g., a thrombus, a drug delivery catheter can be delivered via the guidewire to the feature, and a photosensitive therapeutic can be administered and subsequently photoactivated with the guidewire. Additionally, because the guidewires of the invention are narrower in diameter than typical imaging catheters, the guidewires can be delivered to areas of the body with restricted passages, e.g., occluded arteries.

In an embodiment, the guidewires, methods, and systems of the invention are useful for delivering photosensitive or photoactivated therapeutic agents. Such therapeutic agents are activated, released, transformed, or bound upon exposure to electromagnetic radiation, i.e., light. The light may be microwave, infrared, visible, or ultraviolet light, most typically visible or near ultraviolet. In some embodiments, the light breaks a photocleavable bond in the photoactivated agent, releasing an active agent, e.g., a drug or other therapeutic agent such as an RNAi. The guidewires, methods, and systems of the invention allow a drug that is not stable in a physiological environment to be stabilized for transport to a location for treatment and then released in a potent form in proximity to the location for treatment.

Access guidewires (generally "guidewires" herein) are known medical devices used in the vasculature or other anatomical passageway to act as a guide for other devices, e.g., a catheter. Typically, once access to the anatomical passageway, e.g., an artery, the guidewire is inserted and steered under fluoroscopy (real time x-ray imaging) to the location of interest. Then one or more devices are delivered over the guide wire to diagnose, image, and treat the condition.

Guidewires usually come in diameters of 0.010" to 0.035" with 0.014" being the most common. Guidewires (and other intravascular objects) are also sized in units of French, each French being ⅓ of a mm or 0.013". Guidewire lengths vary up to 400 cm, depending on the anatomy and work flow. The ends of the guidewire are denoted as distal (far from the user, i.e., inside the body) and proximal (near the user, i.e., outside the body). Often a guidewire has a flexible distal tip portion about 3 cm long and a slightly less flexible portion about 30 to 50 cm long leading up to the tip with the remainder of the guidewire being stiffer to assist in maneuvering the guidewire through tortuous vasculature, etc. The tip of a guidewire typically has a stop or a hook to prevent a guided device, e.g., a catheter from passing beyond the distal tip. In some embodiments, the tip can be deformed by a user to produce a desired shape.

Advanced guidewire designs include sensors that measure flow and pressure, among other things. For example, the FLOWIRE® Doppler Guide Wire, available from Volcano Corp. (San Diego, Calif.), has a tip-mounted ultrasound transducer and can be used in all blood vessels, including both coronary and peripheral vessels, to measure blood flow velocities during diagnostic angiography and/or interventional procedures.

The proximal end of a guidewire varies depending upon the complexity of the device. Simple guidewires, used for placement of devices such as catheters, are untethered, i.e., the proximal end does not need to be connected to other equipment. Sensing guidewires, on the other hand, require a signal connection when the sensor is used. The signal connection is typically detachable to facilitate loading/unloading catheters, however it is also possible to load a rapid exchange catheter on a guidewire prior to guidewire insertion. Placement guidewires without tethers are less expensive and most useful when a procedure requires multiple catheter exchanges, because each catheter can be quickly removed from the guidewire and the next catheter placed on the guidewire.

While not shown in detail in the figures, a guidewire of the invention has a tethered proximal end, typically with a detachable connection. As discussed below, guidewires of the invention use optical fibers to supply light to the distal end of the guidewire and to detect returning light. Accordingly, guidewires of the invention have a tether comprising optical fibers and one or more detachable optical couplings. In some embodiments, all of the optical fibers of the guidewire are coupled into a single optical coupling. The tethers may additionally comprise electrical connections as needed to produce acoustic energy or to receive acoustic echoes.

Additionally, while not shown in detail in the figures, a guidewire of the invention has a mid-body connecting the proximal and distal ends. The mid-body is typically a length between 50 and 500 cm, typically greater than or equal to 100 cm, typically less than or equal to 400 cm, typically about 200 to 300 cm. The mid-body typically has a core, which is typically a biocompatible and resilient metal wire. The core may comprise multiple strands of metal fiber or the core may be a unitary piece of metal wire. The core is typically constructed from nitinol or stainless steel. As discussed in greater detail below, the mid-body will also comprise a number of optical fibers to deliver light to the distal end of the guidewire and to return reflected light. The optical fibers may be bound to the core with adhesive or fasteners. The optical fibers may be touching the core or the optical fibers may be displaced axially from the core with spacer, typically a resilient polymer. The core and the optical fibers (and optionally spacer) are coated with a coating to help the guidewire pass through an introducer, to pass through the vasculature, and to help delivered devices (e.g., catheter) easily pass over the guidewire. In addition to being both biocompatible and resilient (will not dislodge or flake), the guidewire coating is typically lubricious to reduce the friction between the guidewire and a catheter.

The distal end of an embodiment of a guidewire 100 is depicted in FIG. 1A. The guidewire 100 comprises a first optical fiber 110 and a second optical fiber 130. Optical fibers 110 and 130 may be constructed from glass or plastic. The first optical fiber 100 and the second optical fiber 130 both include blazed Bragg gratings 115 and 135 (discussed below). In the embodiment shown in FIG. 1A, the blazed Bragg grating 115 of the first optical fiber 110 is in proximity to an ultrasound transducer 120. The blazed Bragg grating 135 of the second optical fiber 130 is in proximity to a lens 140. The guidewire 100 terminates in a tip 150. The core of the guidewire is not shown in FIG. 1A to assist clarity, however, a core is typically present in a guidewire as shown in FIG. 1A.

The guidewires of the invention employ fiber Bragg gratings to couple light into or out of optical fibers 110 and 130. A fiber Bragg grating is a periodic modulation of the index of refraction in a fiber. If the periodicity, d, of the modulation satisfies the Bragg condition ($d=n\lambda/2$) for a wavelength $\lambda$, that wavelength will be reflected. That is, the fiber Bragg grating acts as a wavelength selective mirror. The degree of index change and the length of the grating influences the ratio of light reflected to that transmitted through the grating. A review of fiber Bragg gratings can be found at A. Othonos, *Rev. Sci. Inst.*, 68 (12), 4309 (1997), incorporated by reference herein in its entirety. First and second optical fibers 110 and 130 may comprise a normal Bragg grating (back reflective—not shown in FIG. 1A) in addition to blazed Bragg gratings (angle reflective) 115 and 135. Blazed Bragg gratings are discussed in greater detail in Othonos, referenced above.

As shown in FIG. 1B, the blazed Bragg gratings couple light, 160 and 170, from the first and second optical fibers, 110 and 130, out of the fibers and into an ultrasound transducer 120 and/or a lens 140. The light 160 and 170 originates in the same or different not sources, discussed in detail below. The light 160 and 170 may be of different wavelengths, or the light 160 and 170 may be of the same wavelength. As shown in FIG. 1B, the light 160 coupled out of the first optical fiber 110 by the blazed Bragg grating 115 will impinge on the ultrasound transducer 120 producing ultrasonic waves 180. The light 170 coupled out of the second optical fiber 130 by the blazed Bragg grating 135 will impinge on the lens 140 coupling electromagnetic waves 190 out of the guidewire 100. Accordingly, the guidewire 100 can provide acoustic waves 180 for ultrasound imaging or Doppler measurements and electromagnetic waves 190 for activating photoreactive therapeutic agents.

The ultrasound transducer 120 comprises an optically-absorptive photoacoustic material, which produces ultrasound waves 180 when it absorbs light 160. The optically absorptive photoacoustic material is positioned, with respect to the blazed Bragg grating 115, to receive the optical energy leaving the blazed grating. The optically absorptive photoacoustic material is selected to absorb light 160, and produce and transmit ultrasound or other acoustic waves for acoustic imaging of a region of interest about the distal tip of the guidewire 100.

In preferred embodiments, the incident light 160 is pulsed at a frequency at which the acoustic waves will be produced. Light sources that produce pulses at ultrasonic frequencies, e.g., 1 MHz and greater, are commercially-available, typically solid state lasers. Nonetheless, photoacoustic materials have natural acoustic resonances, and the photoacoustic material will naturally produce a spectrum of acoustic frequencies when the material absorbs the incident light 160 and the photoacoustic material relaxes by producing acoustic waves. If it is desired to rely on the natural frequencies of the photoacoustic material, the incident light 160 may be continuous.

In an embodiment, the photoacoustic material has a thickness in the direction of propagation that increases the efficiency of emission of acoustic energy. In some embodiments, the thickness of the photoacoustic material is selected to be about one fourth of the acoustic wavelength of the material at the desired acoustic frequency ("quarter wave matching"). Providing photoacoustic material with quarter wave matching improves the generation of acoustic energy by the photoacoustic material, resulting in improved ultrasound images. Using the quarter wave matching and sensor shaping techniques, the productivity of the fiber blazed Bragg sensor and photoacoustic materials approaches the productivity of piezoelectric transducers known in the field of ultrasound imaging.

In one embodiment, before the photoacoustic transducer is fabricated, the guidewire 100 is assembled, such as by binding the optical fibers 110 and 130 to the core (not shown) and tip 150, and optionally coating the guidewire 100. The photoacoustic transducer 120 is then integrated into the guidewire 100, by etching or grinding a groove in the assembled guidewire 100 above the intended location of the blazed Bragg grating 115 in the first optical fiber 110. As discussed above, the depth of the groove in the assembled guidewire 100 may play a role in the efficiency of the acoustic wave production (e.g., quarter wave matching).

After the photoacoustic transducer 120 location has been defined, the blazed Bragg grating 115 can be added to the first optical fiber 110. In one example, the grating 115 is created using an optical process in which the portion of the first optical fiber 110 is exposed to a carefully controlled pattern of UV radiation that defines the blazed Bragg grating 115. After the blazed Bragg grating is complete, a photoacoustic material is deposited or otherwise added over the blazed Bragg grating 115 to complete the transducer 120. An exemplary photoacoustic material is pigmented polydimethylsiloxane (PDMS), such as a mixture of PDMS, carbon black, and toluene. The photoacoustic materials may naturally absorb the light 160, or the photoacoustic material may be augmented with dyes, e.g., organic dyes, or nanomaterials (e.g., quantum dots) that absorb light 160 strongly. The photoacoustic material can also be "tuned" to selectively absorb specific wavelengths by selecting suitable components.

The acoustic waves generated by the photoacoustic material interact with tissues (e.g., vasculature) in the vicinity of the distal end of the guidewire 100, and are reflected back (echoes). The reflected acoustic waves are collected and analyzed to obtain information about the distance from the tissues to the guidewire, or the type of tissue, or other information, such as blood flow or pressure. The guidewires 200 and 250, shown in FIGS. 2A and 2B, provide alternative mechanisms for collecting the reflected acoustic waves for analysis with detectors and signal processing equipment connected to the proximal end of the guidewire.

In a first embodiment, shown in FIG. 2A, the guidewire 200 additionally includes a third optical fiber 220 with a blazed Bragg grating (not shown) and a photoreflective material 230 in communication with the blazed Bragg grating and the exterior of the guidewire 200. The photoreflective member is flexibly resilient, and is displaced by acoustic waves reflected by the tissues. A transparent (or translucent) flexible material is disposed between the third optical fiber 220 and the photoreflective material 240, thereby allowing a deflection in the photoreflective material 240 to change the path length of the light between the third optical fiber 220 and the photoreflective material 230. In alternative embodiments, a void can be left between the third optical fiber 220 and the photoreflective material 240.

In the absence of incident acoustic energy, the photoreflective material will be in a neutral position, providing a baseline path length between the third optical fiber 220 and the photoreflective material 230. Incident light, transmitted via the third optical fiber 220, will be reflected from the photoreflective material 230, and return to a detector at the proximal end of guidewire 200 (not shown) with a characteristic round trip time. The light transmitted via the third optical fiber 220 may be the same light as used to produce acoustic energy (discussed above), the same light used to photoactivate therapeutics (discussed above), or a different light (wavelength, pulse frequency, etc.). When the photoreflective material 230 is deflected, e.g., with the absorbance of incident acoustic waves, the path length between the third optical fiber 220 and the photoreflective material 230 will change, resulting in a measurable change in the properties of the reflected as measured by a detector at the proximal end of guidewire 200 (not shown). The change may be a shift in the time of the return trip, or the shift may be an interferometric measurement. The change in the properties of the reflected light can then be analyzed to determine properties of the tissues from which the acoustic waves were reflected.

In another embodiment, shown in FIG. 2B, the first optical fiber 110 is modified to include first and second normal Bragg gratings, 260 and 265. First and second normal Bragg gratings, 260 and 265, which are partially and mostly reflective, respectively, create a resonant cavity in first optical fiber 110. In the absence of incident acoustic energy, light in the resonant cavity will have a characteristic return signature, e.g., an optical decay signal. With the incidence of reflected acoustic energy, the path length and/or path direction of the resonant cavity will be modified, leading to a change in the return signature. By monitoring changes in the return signature, it is possible to determine the timing of reflected acoustic signals, and hence, properties of the tissues from which the acoustic waves were reflected. The detection is similar to known methods of detecting strain or temperature changes with optical fibers.

In one example of operation, light reflected from the blazed grating 115 excites the photoacoustic material 120 in such a way that the optical energy is efficiently converted to substantially the same acoustic frequency for which the resonant cavity sensor is designed. The blazed Bragg grating 115 and the photoacoustic material 120, in conjunction with the resonant sensor, provide both an acoustic transducer and a receiver, which are harmonized to create an efficient unified optical-to-acoustic-to-optical transmit/receive device. In some embodiments, more than one type of light (e.g., wavelength) can be coupled into the same fiber, allowing one to be used to produce the acoustic wave and another to monitor reflected acoustic waves. In a further example, the optical transmit/receive frequencies are sufficiently different that the reception is not adversely affected by the transmission, and vice-versa.

Cross sectional view of guidewires 200 and 250 are shown in FIGS. 3A and 3B. As in FIGS. 1A-2B, the core has been left out for clarity. FIG. 3A shows a cross section taken at detail AA in FIG. 2A, including first, second, and third optical fibers, 110, 130, and 220. FIG. 3A also included a fourth optical fiber 225, which is not shown in FIG. 2A. As shown in FIG. 3A, the photoacoustic material 120, the lens 140, and the photoreflective material 240 are substantially in communication with the exterior of the guidewire and the respective optical fibers. The dashed line in the photoreflective material 240 is intended to show the extent of possible deflection of the photoreflective material. FIG. 3B shows a cross section taken at detail BB in FIG. 28, including first and second optical fibers, 110 and 130. As shown in FIG. 3B, the photoacoustic material 120 and the lens 140 are substantially in communication with the exterior of the guidewire and the respective optical fibers.

In preferred embodiments, guidewires of the invention will comprise a plurality of optical fibers as well as arrays of acoustic transducers, acoustic receivers, and lenses for delivering electromagnetic radiation. Cross-sections of an exemplary guidewire 400 including multiple fibers, transducers, receivers, and lenses are depicted in FIGS. 4A and 4B. FIG. 4A shows a cross-section taken toward the proximal end of guidewire 400. Toward the proximal end, guidewire 400 includes optical fibers 410 which couple light from a source at the proximal end of the guidewire 400 to the photoacoustic materials, photoreflective materials, and lenses at the distal end of the guidewire. As shown in FIG. 4A, the fibers surround a core 450 which provides the structural qualities of the guidewire. The fibers 410 are additionally stabilized with a spacer material 460, and the entire guidewire is covered with a lubricious coating 470 to facilitate delivery of other devices, e.g., catheters over the guidewire.

The corresponding distal end of the guidewire 400 shown in FIG. 4A is shown in FIG. 4B. The guidewire 400 includes a plurality of photoacoustic materials 420, described in detail above, that produce acoustic waves for imaging. The guidewire 400 also includes a plurality of lenses 440 that couple electromagnetic radiation out of the optical fibers to photoactivate therapeutics. As shown in FIG. 4B, the guidewire comprises a plurality of photoreflective materials 430 that act as receivers of acoustic energy, allowing the detection of acoustic waves reflected from the surrounding tissues. The guidewire 400 allows for imaging and photoactivation around the circumference of the guidewire 400. In some embodiments, the guidewire may rotated during the imaging in order to provide improved image quality and to avoid blind spots due to the configuration of the acoustic transducers and receivers.

In some embodiments, as shown in FIG. 5A, a plurality of photoacoustic materials 520, photoreflective materials 530, and lenses 540 can be arrayed at the distal end of a guidewire 500. The array allows a wider field of view and photoactivation. Additionally, by staggering the elements, e.g., the photoacoustic materials 520, photoreflective materials 530, and lenses 540, the guidewire 500 provides more complete radial coverage. In alternative embodiments, as shown in FIG. 5B, a plurality of photoacoustic materials 520 and lenses 540 can be arrayed in a guidewire 550. In the embodiment shown in FIG. 5B, the fibers coupled to the photoacoustic materials 520 would have both blazed and normal Bragg grating, thereby allowing the fibers associated with photoacoustic materials 520 to act as the source of acoustic energy and to receive acoustic energy reflected from the surrounding tissue.

The guidewires described will typically be used as part of a system. An exemplary system 600 is shown in FIG. 6. The system includes a guidewire 610 having optical fibers 612 and 614 coupled to the proximal end, allowing one or more sources of light 620 and 630 to be coupled into the optical fibers. Two optical fibers, such as 616 and 618, may be coupled into a single fiber, such as 614, to facilitate signal production and detection. The source light and the signal light may be coupled or split with fiber couplers, dichroic, and filter as necessary to achieve the desired performance. Additionally, while multiple light sources are shown in system 600, it should be understood that in some embodiments a system can work with only one light source. Furthermore, a particular fiber need not be limited to a single light source as some fibers can support multiple wavelengths simultaneously and the wavelengths can be separated for analysis using known multiplexing techniques.

The sources of light 620 and 630 for the system 600 may be any known light source capable of producing light with the desired temporal and frequency characteristics. Sources 620 and 630 may be, for example, solid-state lasers, gas lasers, dye lasers, or semiconductor lasers. Sources 620 and 630 may also be LED or other broadband sources, provided that the sources are sufficiently powerful to drive the photoacoustic transducers and to photoactivate the therapeutics. In some instances the sources 620 and 630 are gated to provide the needed temporal resolution. In other instances, the sources 620 and 630 inherently provide short pulses of light at the desired frequency, e.g., 20 MHz.

A detector 640, coupled to fiber 616 is used to measure changes to the coupled light to determine how the acoustic environment of the guidewire 610 is changing. The detector may be a photodiode, photomultiplier tube, charge coupled array, microchannel detector, or other suitable detector. The detector may directly observe shifts in return light pulses, e.g., due to deflection of the photoreflective material, or the detector may observe interferometric changes in the returned light due to changes in pathlength or shape. Fourier transformation from time to frequency can also be used to improve the resolution of the detection.

As shown in FIG. 6, a controller 650 will be used to synchronize the sources 620 and 630 and the detector 640. The controller may maintain system synchronization internally, or the system may be synchronized externally, e.g., by a user. In some embodiments, the acoustic production and detection can be synchronized through source 620 and detector 640 and source 630 is used to photoactivate therapeutics at a desired time.

The output of the detector 640 will typically be directed to image processing 660 prior to being output to a display 670 for viewing. The image processing may deconvolve the reflected light to produce distance and/or tissue measurements, and those distance and tissue measurements can be used to produce an image, for example an intravascular ultrasound (IVUS) image. The image processing may additionally include spectral analysis, i.e., examining the energy of the returned acoustic signal at various frequencies. Spectral analysis is useful for determining the nature of the tissue and the presence of foreign objects. A plaque deposit, for example, will typically have a different spectral signature than nearby vascular tissue without such plaque, allowing discrimination between healthy and diseased tissue. Also a metal surface, such as a stent, will have a different spectral signal. Such signal processing may additionally include statistical processing (e.g., averaging, filtering, or the like) of the returned ultrasound signal in the time domain. Other signal processing techniques known in the art of tissue characterization may also be applied.

Other image processing may facilitate use of the images or identification of features of interest. For example, the border of a lumen may be highlighted or plaque deposits may be displayed in a visually different manner (e.g., by assigning plaque deposits a discernible color) than other portions of the image. Other image enhancement techniques known in the art of imaging may also be applied. In a further example, similar techniques are used for discriminating between vulnerable plaque and other plaque, and enhancing the displayed image provide a visual indicator assisting the user in discriminating between vulnerable and other plaque. Other measurements, such as flow rates or pressure may be displayed using color mapping or by displaying numerical values.

Figure 7:
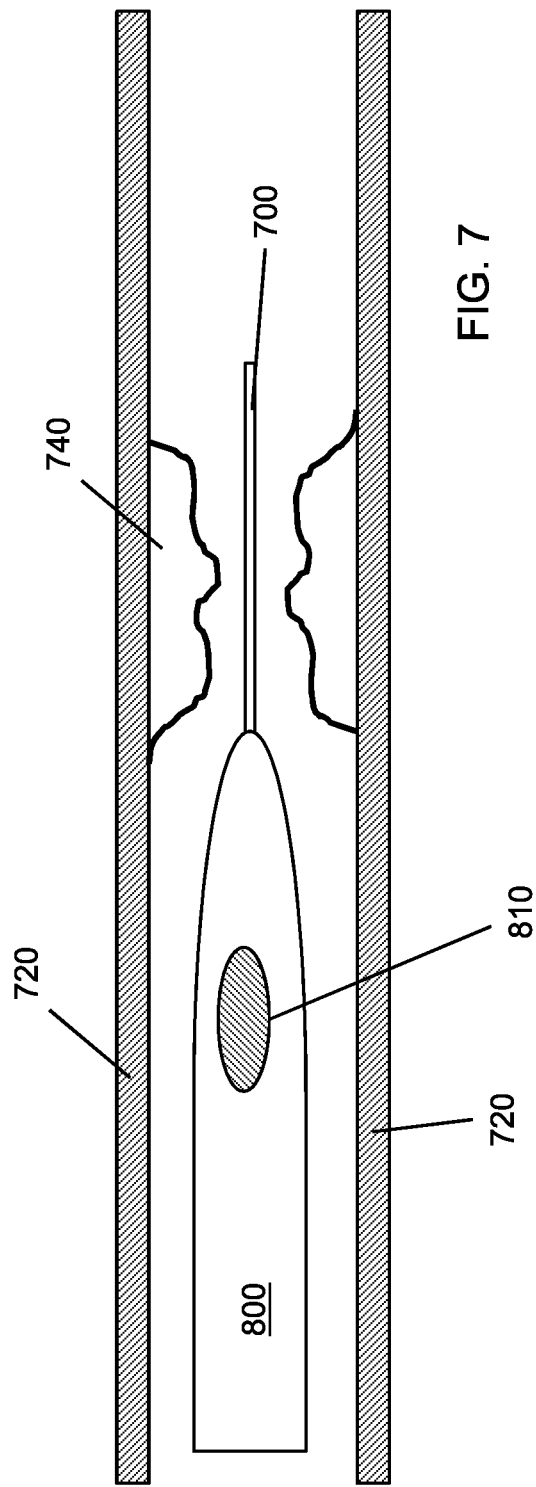
FIG. 7 shows an exemplary use of a guidewire of the invention with a drug delivery catheter for delivering therapy to a thrombus.
Figure 8:
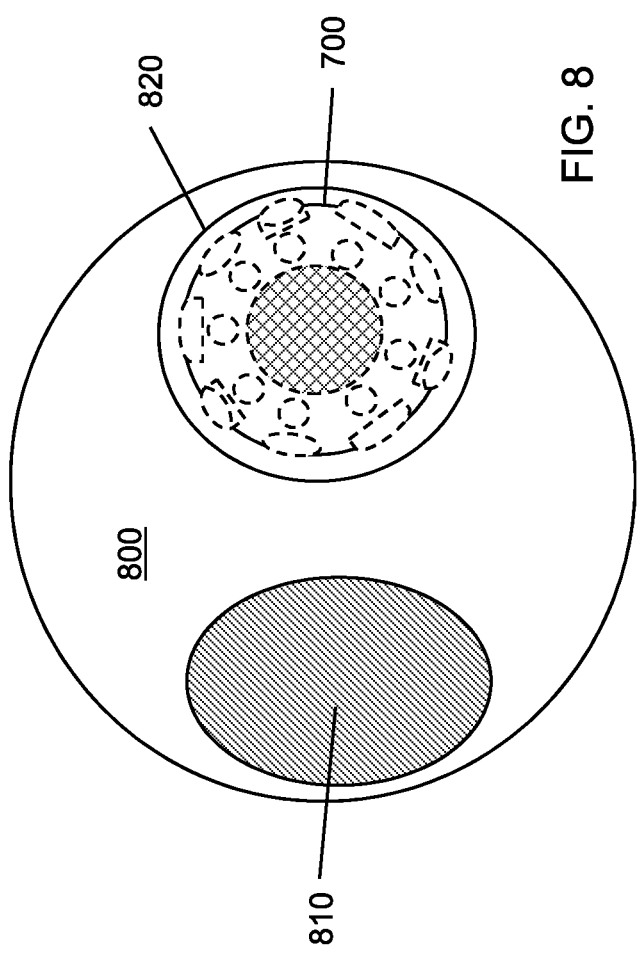
FIG. 8 depicts the end view of a drug delivery catheter used with an embodiment of a guidewire.

The use of a guidewire 700 of the invention in combination with a drug delivery catheter 800 is shown in FIGS. 7 and 8. FIG. 7 illustrates a longitudinal cross-sectional view of a vessel, having vessel walls 720, defining a lumen. In the example described in FIG. 7, the vessel is occluded with a thrombus 740. After entry into the patient, a guidewire 700 is directed past the thrombus, allow the thrombus, and tissues past the thrombus, to be imaged. Using guidewire 700 the thrombus 740 can be identified for treatment with a photoactivated therapeutic, e.g., a thrombolytic agent. A drug delivery catheter 800, having a lumen 820 (shown in FIG. 8) for following guidewire 700, can be delivered as near as safe to thrombus 740. Once in position, a photoactivated therapeutic can be delivered via an opening 810 in the drug delivery catheter 800 in fluid communication with the proximal end of the catheter 800. Once delivered, the photoactivated therapeutic can be activated with electromagnetic radiation delivered from the guidewire 700. During and after treatment, the tissue can be monitored using the imaging capabilities of the guidewire 700, discussed above.

While FIG. 7 shows delivery of a therapeutic to a thrombus, it should be realized that the guidewires, methods and systems described are well suited for delivering therapeutics to many types of tissues. For example, an antiangiogenic drug, such as paclitaxel, can be deactivated for transport to the vicinity of a tumor in the lung. Once delivered to the tumor, e.g., with a drug delivery catheter, the deactivated therapeutic can be photoactivated, releasing concentrated paclitaxel in a potent form in proximity to the tumor. Thus, only the tumor and the immediately surrounding tissues will be exposed to the powerful antiangiogenic agent.

The same principles can be applied to a variety of classes of drugs, such as thrombolytic agents, anti-cancer agents, anti-inflammatory agents, analgesic agents, or combinations thereof. For example, the activated agent may comprise streptokinases, anistreplases, urokinases, tissue plasminogen activators (t-PA), alteplases, tenecteplases, or reteplases. A photoactivated agent used with guidewires, methods, and systems of the invention may comprise more than one activated agent or more than one class of activated agent. For example, a photoactivated agent may comprise a thrombolytic drug and an anti-coagulant, such as heparin.

The guidewires, methods, and systems of the invention may be used in the treatment of a number of disorders in a subject. For example, the guidewires, methods, and systems can be used to treat a variety of vascular diseases, including, but not limited to, atherosclerosis, ischemia, coronary blockages, thrombi, occlusions, stenosis, and aneurysms. The guidewires, methods, and systems can be used to access and treat a large number of locations that are accessible via the vasculature or urological or reproductive tracts. Such locations include the heart, brain, lungs, liver, kidneys, prostate, ovaries, testes, gallbladder, pancreas, and lymph nodes, among other locations. The guidewires, methods, and systems can be used to treat a variety of diseases, including cardiovascular disease, cancer, inflammatory disease (e.g., autoimmune disease, arthritis), pain, and genetic disorders.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A guidewire comprising:
a first optical fiber comprising a first blazed Bragg grating being at least partially reflective of a first wavelength of electromagnetic radiation;
a photoacoustic imaging element comprising photoacoustic material disposed along a first sidewall portion of the guidewire and in photocommunication with the first blazed Bragg grating and configured to image a treatment site within a subject using acoustic energy generated in response to incidence of the first wavelength of electromagnetic radiation, wherein the photoacoustic imaging element directs the acoustic energy laterally from the guidewire in a first direction;
a second optical fiber comprising a second blazed Bragg grating being at least partially reflective of a second wavelength of electromagnetic radiation;
a lens spaced from the photoacoustic imaging element and disposed along a second sidewall portion of the guidewire in proximity to the second blazed Bragg grating and in photocommunication with the second blazed Bragg grating and an exterior of the guidewire such that the lens is configured to receive the second wavelength of electromagnetic radiation from the second blazed Bragg grating and to direct the second wavelength of electromagnetic radiation laterally from the guidewire in a second direction to activate a photosensitive therapeutic agent at the treatment site, based on imaging the treatment site with the acoustic energy;
a third optical fiber comprising a third blazed Bragg grating being at least partially reflective of a third wavelength; and
a photoreflective member comprising a photoreflective material different from the photoacoustic material, wherein the photoreflective material is disposed along a third sidewall portion of the guidewire in proximity to the third blazed Bragg grating and in photocommunication with the third blazed Bragg grating, wherein at least some of the photoreflective material forms a portion of the exterior of the guidewire.

2. The guidewire of claim 1, wherein the photoacoustic imaging element is in acoustic communication with the exterior of the guidewire.

3. The guidewire of claim 2, wherein photo absorption of the first wavelength by the photoacoustic imaging element creates acoustic waves in proximity to the guidewire.

4. The guidewire of claim 1, wherein an absorbance of incident acoustic waves in proximity to the guidewire by the photoreflective member cause a deflection of the photoreflective member toward an interior of the guidewire.

5. The guidewire of claim 4, wherein the deflection of the photoreflective member creates a change in a pathlength for the third wavelength between the third blazed Bragg grating and the photoreflective member.

6. The guidewire of claim 4, wherein the deflection of the photoreflective member creates a change in a property of a portion of the third wavelength reflected by the third blazed Bragg grating, wherein the change is measurable by an interferometric measurement.

7. The guidewire of claim 1, wherein the first and second wavelengths are the same.

8. The guidewire of claim 1, wherein the first and third wavelengths are different.

9. The guidewire of claim 8, wherein the second and third wavelengths are the same.

10. The guidewire of claim 1, further comprising a strengthening member to support the guidewire.

11. The guidewire of claim 1, wherein the second wavelength is capable of activating a therapeutic agent.

12. The guidewire of claim 1, further comprising a plurality of photoacoustic imaging elements and a plurality of lenses arranged in alternating fashion about a circumference of the guidewire.

13. The guidewire of claim 1, further comprising a plurality of photoacoustic imaging elements and a plurality of lenses arranged to form a staggered array such that photoacoustic imaging elements and lenses alternate both along a length of the guidewire and about a circumference of the guidewire.

14. A method of treating a subject, comprising:
directing electromagnetic radiation comprising a first wavelength onto a photoacoustic element comprising photoacoustic material and disposed along a first sidewall portion of a guidewire to generate acoustic energy, wherein the photoacoustic element directs the acoustic energy laterally from the guidewire in a first direction;
imaging a subject with the acoustic energy produced from the guidewire;
administering a photosensitive therapeutic agent to the subject;
activating the photosensitive therapeutic agent with electromagnetic radiation via directing electromagnetic radiation comprising a second wavelength through a lens spaced from the photoacoustic element and disposed along a second sidewall portion of the guidewire, wherein the lens directs the second wavelength laterally from the guidewire in a second direction; and
determining at least one property of a tissue imaged with the acoustic energy based at least in part on analysis of electromagnetic radiation returned from a photoreflective element comprising photoreflective material different from the photoacoustic material and disposed along a third sidewall portion of the guidewire, wherein at least some of the photoreflective material forms a portion of an exterior of the guidewire.

15. The method of claim 14, wherein the guidewire comprises:
a first optical fiber comprising a first blazed Bragg grating being at least partially reflective of the first wavelength;
the photoacoustic element that absorbs the first wavelength and is in photocommunication with the first blazed Bragg grating;
a second optical fiber comprising a second blazed Bragg grating being at least partially reflective of the second wavelength; and
the lens, wherein the lens is disposed in proximity to the second blazed Bragg grating and in photocommunication with the second blazed Bragg grating and the exterior of the guidewire,
wherein the activating the photosensitive therapeutic agent with electromagnetic radiation includes directing the electromagnetic radiation through the lens.

16. The method of claim 15, wherein the photoacoustic element is in communication with the exterior of the guidewire.

17. The method of claim 15, wherein photoabsorption of the first wavelength by the photoacoustic element creates acoustic waves in proximity to the guidewire.

18. The method of claim 15, wherein the guidewire further comprises:
a third optical fiber comprising a third blazed Bragg grating being at least partially reflective of a third wavelength; and
the photoreflective member, wherein the photoreflective member reflects the third wavelength and is in photocommunication with the third blazed Bragg grating.

19. The method of claim 14, wherein the imaging comprises imaging at least a portion of an anatomical system selected from a cardiovascular system, a lymphatic system, a urological system, or a reproductive system.

20. The method of claim 19, wherein the imaging comprises imaging an artery or vein of the cardiovascular system.

21. The method of claim 14, wherein the photosensitive therapeutic agent comprises thrombolytic agents, anti-cancer agents, anti-inflammatory agents, analgesic agents, or combinations thereof.

22. The method of claim 21, wherein the photosensitive therapeutic agent comprises a thrombolytic agent selected from streptokinases, anistreplases, urokinases, tissue plasminogen activators (t-PA), alteplases, tenecteplases, or reteplases.

23. The method of claim 14, wherein the photosensitive therapeutic agent comprises a nucleic acid.

24. The method of claim 14, wherein the administering comprises delivering the photosensitive therapeutic agent to a tissue within the subject with a drug-delivery catheter.

25. A system for administering a photosensitive therapeutic agent to a subject, comprising:
a guidewire, comprising:
a first optical fiber comprising a first blazed Bragg grating being at least partially reflective of a first wavelength of electromagnetic radiation,
a photoabsorptive member comprising photoacoustic material that is disposed along a first sidewall portion of the guidewire and in photocommunication with the first blazed Bragg grating and is configured to absorb the first wavelength of electromagnetic radiation and to generate acoustic energy, wherein the photoabsorptive member directs the acoustic energy laterally from the guidewire in a first direction,
a second optical fiber comprising a second blazed Bragg grating being at least partially reflective of a second wavelength of electromagnetic radiation,
a lens spaced from the photoabsorptive member and disposed along a second sidewall portion of the guidewire in proximity of the second blazed Bragg grating and in photocommunication with the second blazed Bragg grating and an exterior of the guidewire such that the lens is configured to receive the second wavelength of electromagnetic radiation from the second blazed Bragg grating and to direct the second wavelength of electromagnetic radiation laterally from the guidewire in a second direction,
a third optical fiber comprising a third blazed Bragg grating being at least partially reflective of a third wavelength, and
a photoreflective member comprising a photoreflective material different from the photoacoustic material, wherein the photoreflective material is disposed along a third sidewall portion of the guidewire in proximity to the third blazed Bragg grating and in photocommunication with the third blazed Bragg grating, wherein at least some of the photoreflective material forms a portion of the exterior of the guidewire;
a first source of the first wavelength of electromagnetic radiation optically coupled to the first optical fiber;
a second source of the second wavelength of electromagnetic radiation optically coupled to the second optical fiber; and
a controller coupled to the first source and the second source, wherein the controller is operable to:
control the first source to direct the first wavelength of electromagnetic radiation such that the photoabsorptive member generates the acoustic energy;
image a treatment site within the subject with the generated acoustic energy; and
control the second source to direct the second wavelength of electromagnetic radiation to activate the photosensitive therapeutic agent at the treatment site with the second wavelength of electromagnetic radiation, based on the imaging of the treatment site with the generated acoustic energy.

26. The system of claim 25, wherein the first and second wavelengths are the same.

27. The system of claim 25, wherein the source of the first wavelength and the source of the second wavelength is the same source.

28. The system of claim 25, wherein the first and third wavelengths are the same.

29. The system of claim 25, further comprising a drug delivery catheter comprising a lumen compatible with the guidewire.

* * * * *